(12) United States Patent
Vittal et al.

(10) Patent No.: US 7,049,459 B2
(45) Date of Patent: May 23, 2006

(54) 1-[(4-METHYL THIO)PHENYL]-2-(PHENYL ACETOXY)-1-ETHANONE AND A PROCESS FOR PREPARING THE SAME

(75) Inventors: Tangiraja Venkata Subramanya Krishna Vittal, Andra Pradesh (IN); Mudduluru Hari Krishna, Andra Pradesh (IN)

(73) Assignee: Shasun Chemicals and Drugs Limited, Tamil Nadu (IN)

( * ) Notice: Subject to any disclaimer, the term of this patent is extended or adjusted under 35 U.S.C. 154(b) by 4 days.

(21) Appl. No.: 10/491,579

(22) PCT Filed: Oct. 10, 2001

(86) PCT No.: PCT/IN01/00176

§ 371 (c)(1), (2), (4) Date: Apr. 2, 2004

(87) PCT Pub. No.: WO03/030812

PCT Pub. Date: Apr. 17, 2003

(65) Prior Publication Data

US 2004/0242680 A1     Dec. 2, 2004

(51) Int. Cl.
C07C 321/00 (2006.01)
C07C 69/76 (2006.01)
C07C 49/76 (2006.01)
C07D 407/00 (2006.01)
C07D 305/12 (2006.01)

(52) U.S. Cl. .......... 560/9; 560/105; 549/302; 549/326; 568/308; 568/331

(58) Field of Classification Search .......... 560/9, 560/105; 568/308, 331; 549/302, 326
See application file for complete search history.

(56) References Cited

FOREIGN PATENT DOCUMENTS

WO    WO98/00416    *   1/1998

* cited by examiner

Primary Examiner—Cecilia J. Tsang
Assistant Examiner—Taylor Victor Oh
(74) Attorney, Agent, or Firm—Allen, Dyer, Doppelt, Milbrath & Gilchrist, P.A.

(57) ABSTRACT

This invention relates to 1-[(4-methyl thio)phenyl]-2-(phenyl acetoxy)-1-ethanone. This compound is convertible into 4-(4-methyl thio phenyl)-3-phenyl-2 (5H)-furanone by an economically viable process. This substituted furanone is an intermediate or starting compound for synthesising COX II inhibitor Rofecoxib. This invention also includes a process for preparing the ethanone derivative by halogenating methyl thio aceto phenone and coupling the resulting 2 halosubstituted ethanone with sodium salt of phenyl acetic acid to obtain 1-[(4-methyl thio) phenyl]-2-(phenyl acetoxy)-1-ethanone.

7 Claims, No Drawings

1-[(4-METHYL THIO)PHENYL]-2-(PHENYL ACETOXY)-1-ETHANONE AND A PROCESS FOR PREPARING THE SAME

BACKGROUND OF THE INVENTION

Non-steroid, anti-inflammatory drugs exert most of their anti inflammatory, analgesic and antipyretic activity and inhibit hormone-induced uterine concentrations and certain types of cancer growth through the inhibition of prostaglandin G/H synthase, also known as cyclooxygenase. Until recently, only one form of cyclooxygenease had been characterised, this corresponding to cyclooxygenase I or the constitutive enzyme, as originally identified in bovine seminal vesicles. Recently the gene for a second inducible form of cyclooxygenase (cyclooxygenase-2) has been cloned, sequenced and characterised from chicken, murine and human sources. This enzyme is distinct from the cyclooxygenease-1 which has now also been cloned, sequenced and characterised from sheep, murine and human sources. The second form of cyclooxygenase, cyclooxygenase-2 is rapidly and readily inducible by a number of agents including mitogens, endotoxins, hormones, cytokines and growth factors. As prostaglandines have both physiological and pathological roles, it was concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast it was also concluded that the inducible form of cyclooxygenase-2 is mainly responsible for the pathological affects of prostaglandins where rapid induction of the enzyme would occur in response to such agents as inflammatory agents, hormones, growth factors and cytokines. Thus, a selective inhibitor of cyclooxygenase-2 will have similar anti inflammatory, antipyretic and analgesic properties to a conventional non-steroidal anti inflammatory drug and in addition would inhibit hormone-induced uterine contractions and have potential anti cancer effects but will have a diminished ability to induce some of the mechanism based side effects. In particular such a compound should have a reduced potential for gasterointestinal toxicity, a reduced potential for renal side effects, a reduced effect on bleeding tomes and possibly a lessened ability to induce attacks of asthma in aspirin-sensitive asthmatic subjects.

4-(4-methyl thio phenyl)-3-phenyl-2(5H)-furanone of the formula II shown herein below:

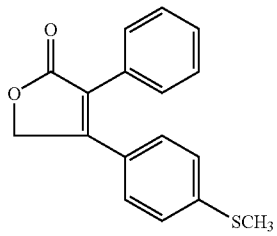

Compound II is a key intermediate in the preparation of COX-II inhibitor, known in the art as Rofecoxib which has a structure X given below:

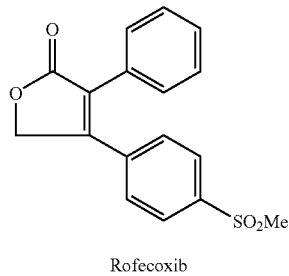

Rofecoxib

The process known in the art for preparing the intermediate compound of the formula II involve tedious multi-step synthesis, utilizing expensive reagents. Therefore, the known synthetic processes for the production of the compound of formula II is not economically viable and are not cost effective.

It has now been found that the novel compound of formula I can be used as a starting material for the production of the compound of formula II in an economically advantageous manner. Cost-effective preparation of this intermediate, no doubt helps in reducing the price line of COX II inhibitor.

DISCLOSURE OF THE INVENTION

This invention encompasses the novel compound 1-[(4-methyl thio) phenyl]-2-(phenyl acetoxy)-1-ethanone which are useful in synthesising an intermediate compound for the production of COX-II inhibitors.

This invention also includes processes for preparing the novel compound of formula I.

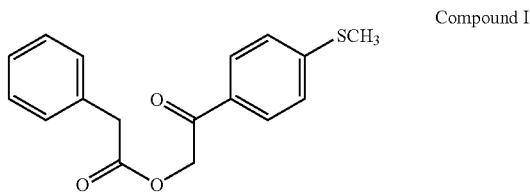

Compound I 4-methylthio acetophenone of the formula III

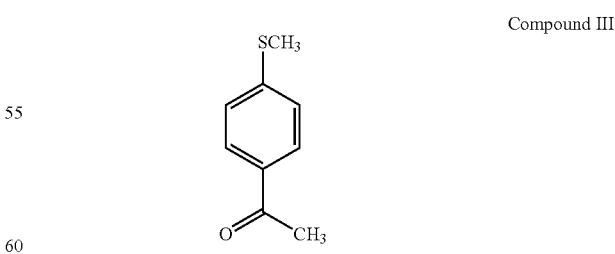

Compound III may be subjected to side chain halogenation to produce the corresponding phenacyl halide which may be coupled with phenyl acetic acid in the presence of organic or inorganic bases to produce the compound of formula I. The reaction scheme is shown below:

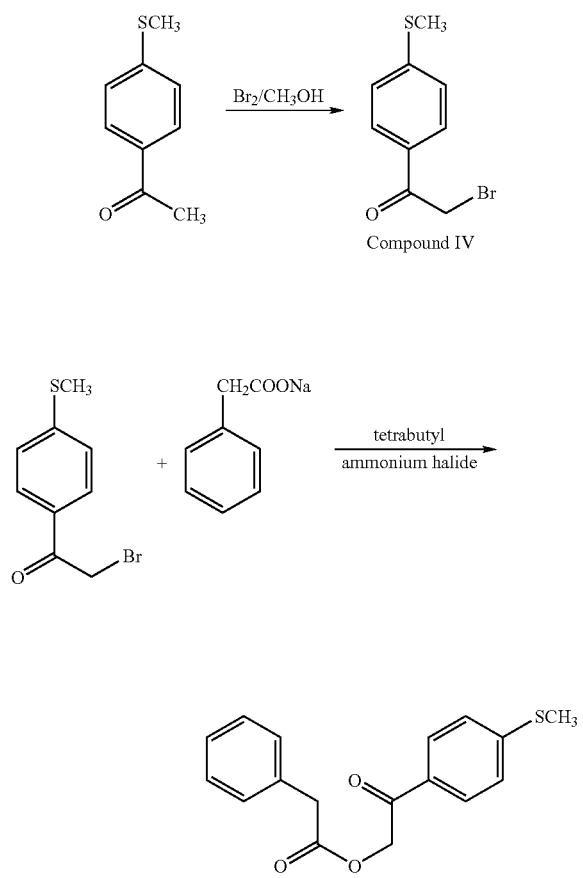

Compound IV

Side chain halogenation reaction of the compound of formula III may be effected in polar protic or polar aprotic solvents in the absence of a catalyst. The halogenation reaction solvents may include chloroform, dichloromethane and carbon tetrachloride and polar protic solvents include methanol, ethanol and isopropanol. Chloroform and methanol are the preferred solvents. Use of acid scavengers in the reaction is purely optional. The acid scavengers when used may include hydroxides, carbonates and bicarbonates of alkali or alkaline earth metals. The preferred acid scavengers are sodium or potassium bicarbonate. The reaction temperature may range from 0° C. to 20° C. and the preferred range is 0° C. to 10° C. It is noted that at 0 to 10° C., the production of the dihalogenated compound is suppressed.

The phenyl halide that separates is filtered and washed with chilled methanol which is preferably cooled below 5° C. The product has excellent purity of 98% and may be used directly for the next step.

Liquid bromine or N-bromo succinamide may be used as the brominating agents. The molar ratio of the reactants may be in the ratio of 1:0.8–1.5-molar equivalents. The preferred range is 1:1.2 molar equivalents. The minimum solvent dilution for carrying out the reaction is in the range of 2–20 times preferably in the range of 5–7 times.

Acid scavengers when used may be in the range of 1–5 times by weight of the compound of formula III. The preferred range is 2–3 times.

The thus obtained phenacyl halide of the formula IV is converted into the compound of formula I by coupling the same with phenylacetic acid in the presence of organic or inorganic bases. The organic bases include di and tri alkyl amines such as di isopropyl amine, tri ethyl amine and 1,8 diazabicyclo [5.4.0] undec-7-ene (DBU). In organic bases include carbonates and bicarbonates of alkaline, or alkaline earth metals. Sodium and potassium carbonates and bicarbonates are preferred. The reaction may be effected in the presence of sodium and/or potassium salts of phenyl acetic acid. A phase transfer catalyst may optionally be used. The preferred phase transfer catalyst is tetraalkyl ammonium halides and tricaprylylmethyl ammonium chloride in polar or non-polar solvents. The polar solvents include DMF, DMA, N-methyl pyrrolidinone, THF and 1,4 dioxane. The non-polar solvents include, aromatic solvents like benzene, toulene, ethyl benzene, isopropyl benzene and isobutyl benzene. The reaction temperature may range from 40 to 100° C. and the preferred range is 70° C. to 100° C. The molar ratio of the reactants namely the compound of formula IV and the phenyl acetic acid sodium salt is in the range of 1.2 molar equivalents and the preferred range is 1:1.0–1.2 molar equivalents. The molar ratio of the compound of formula IV with the phase transfer catalyst is in the range of 1:0.005 to 0.008 molar equivalents. The solvent dilution is generally in the range of 5–25 times over the compound of formula IV and may preferably in the range of 10–15 times.

The Intermediate compound of formula II may be obtained from the compound of formula I by intramolecular knovengal condensation using organic or inorganic bases. The preferred organic bases are trialkyl, dialkyl amines, for example triethyl amine, diisopropyl amine, diethyl methylamine and DBU in polar aprotic solvents. The aprotic solvents include DMF, DMA, N-Methyl pyrrolidinone and acetonitrile etc., preferably DMF or DMA usually in the temperature range of 30° C.–100° C. preferably in the range of 60–90° C. The molar ratio of compound (I) verses the base is 1:10 preferably in the range of 1:1.5–2.5 and with solvent dilution is in the range of 5–25 times over the compound (I) preferably in the range of 5–10 times. The reaction is optionally accompanied by adding the base in portions preferably 3–5 times.

DBU is 1,8 diazabicyclo [5.4.0] undec-7-ene

DMF is dimethyl formamide and

DMA is N,N-dimethyl acetamide.

This invention relates to novel 1-[(4-methyl thio)phenyl]-2-(phenyl acetoxy)-1-ethanone.

This invention also includes a process for the preparation of 1-[(4-methyl thio)phenyl]-2-(phenyl acetoxy)-1-ethanone which comprises the step of halogenating 4-methylthio acetophenone to produce 1-[(4-methyl thio)phenyl]-2 halo ethanone, coupling said 1-[(4-methyl thio)phenyl]-2-haloethanone with sodium salt of phenyl acetic acid to produce 1-[(4-methyl thio)-2-(phenyl acetoxy)1-1-ethanone.

BEST METHOD OF CARRYING OUT THE INVENTION

Procedure for preparing 1-[(4-methyl thio)phenyl]-2-bromo ethanone is given hereinbelow:

4-methyl thio acetophenone (III) (250 g, 1.5 moles) and methanol (1.25 lit) were charged into 3L reaction flask at RT. The resulting mixture was cooled to 0 to 10° C. under stirring. Bromine (244 g, 1.5 moles) was added slowly over a period of 1 hour at 0 to 10° C. The reaction mass was maintained for 30 minutes for at 0 to 10° C. The reaction was monitored by TLC using 30% ethyl acetate in hexane and the stating material absence was observed. The reaction mass pH was adjusted to neutral with NaHCO₃ (250 g) at 0 to 10° C. and the resulting mixture was filtered and washed with chilled methanol (100 ml) followed by chilled water (250 ml). The material was dried at 50° C. under vacuum and the weight of the product obtained is 360 g (98%). The melting range for this compound is 62–64° C.

¹H NMR (300 MHz. CDCl₃):δ 7.88–7.91 (d, 2H, ArH), 7.27–7.30 (d, 2H, ArH), 4.42 (s, 2H, CH₂Br), 2.54 (s, 3H, SCH₃)

Preparation of 1-[(4-methyl thio)phenyl]-2-(phenyl acetoxy)-1-ethanone is given herein below:

Compound IV (250 g, 1.02 moles), phenyl acetic and sodium salt (169 g, 1.06 moles) and Toulene (2.5 liters) were charged into dry 3L reaction flask at RT. 2.5 g of tetrabutyl ammonium iodide was added at room temperature. The resulting mixture was heated to 80 to 90° C. and maintained for 3 hours at the same temperature. The reaction was monitored by TLC using 30% ethyl acetate in hexane and the absence of starting material observed. The reaction mass was cooled to room temperature, filtered, washed with 210 ml of toluene. The filtrate and the washings were combined and distilled in vacuo at 50° C. followed by precipitation with hexane (1 lit). The precipitated solid was filtered and washed with hexane (1 lit), dried thoroughly. The weight of the product obtained was 290 g (95%) and the melting range of the compound (I) was 73–74° C.

¹H NMR (300 MHz. CDCl₃):δ 7.79–7.82 (d, 2H, ArH), 7.25–7.37 (m, 7H, ArH), 5.32 (s, 2H, ArCH₂CO), 3.84 (s, 2H, COCH₂O), 2.53 (s, 3H, SCH₃).

The intermediate compound of formula II for the preparation of COX II inhibitor may be prepared from the novel compound illustrated hereinabove by the following procedure:

Compound (I) (250 gms, 0.83 moles), Diisoproplyamine (210 gms, 2.07 moles) and DMF (1.75 liters) were charges into 3L reaction flask at room temperature under nitrogen. The resulting mixture was heated to 60–70° C. The reaction was monitored by TLC, using 40% ethyl acetate in hexane and the absence of the starting material was observed. The reaction mass diluted with 7 liters of ice water and neutralised with 10 NHCl (250 ml) under stirring and the resulting mixture was filtered and washed with water (5 lit.) and dried. The crude product was dissolved in 2 liters of toluene and the resulting mixture was heated to 80 to 90° C., 5 gram of activated carbon was added to the toluene solution and the mass was filtered. The toluene mother liquor was concentrated to 200 ml, cooled, filtered and the product was washed with 100 ml of toluene. The material was dried under vacuum and the weight of the product obtained was 225 g (95%). The melting range of the product was 141–142° C.

¹H NMR (300 MHz. CDCl₃):δ 7.39–7.44 (m, 5H, ArH), 7.23–7.28 (d, 2H, ArH), 7.15–7.18 (d,2H, ArH), 5.18 (s, 2H, CH₂), 2.49 (s, 3H, SCH₃).

The invention claimed is:

1. 1-[4-methyl thio)phenyl]-2-(phenyl acetoxy)-1-ethanone of the formula I

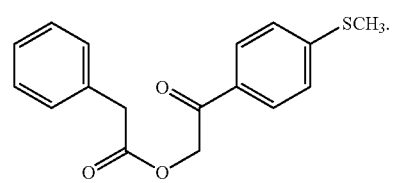

Compound I

2. A process wherein the compound of claim 1 is subjected to an intramolecular condensation in the presence of at least one organic or inorganic base so as to produce compound II

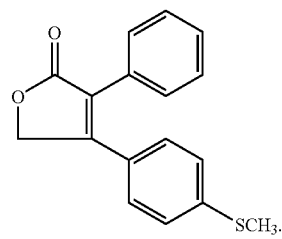

Compound II

3. A process for the preparation of 1-[4-methyl thio)phenyl]-2-(phenylacetoxy)-1-ethanone, the process comprising halogenating 4-methyl thio acetophenone at a temperature of for approximately 0 to 20° C. to produce 1-[(4-methyl thio)phenyl]-2-haloethanone, and coupling said 1[(4-methyl thlo)phenyl]-2-haloethanone in presence of a base and optionally a catalyst selected from tetraalkyl ammonium halides and tricaprylyl methyl ammonium chloride in a solvent at a temperature of approximately 40 to 100° C. with a sodium salt of phenyl acetic acid to produce 1[((4-methylthio)phenyl]-2-(phenyl acetoxy)-1-ethanone.

4. The process of claim 3, wherein halogenating comprises preparing 1[-((4-methyl thio)phenyl]-2-bromoethanone by brominating methyl thio acetophenone and converting said bromoethanone into 1-[(4-methylthio)phenyl]-2-(phenyl acetoxy)-1-ethanone by coupling with phenyl acetic acid in a solution of sodium salts.

5. The process of claim 3 further comprising at least one phase transfer catalyst selected from tetrabutyl ammonium chloride, tetrabutyl ammonium bromide and tetrabutyl ammonium iodide.

6. The process of claim 3 wherein the solvent comprises toluene and a temperature of approximately 80–100° C.

7. The process of claim 5, wherein said catalyst is present in approximately from 0.005 to 0.008 molar equivalents of the 4-methyl thio acetophenone.

* * * * *

UNITED STATES PATENT AND TRADEMARK OFFICE
CERTIFICATE OF CORRECTION

PATENT NO.         : 7,049,459 B2                                    Page 1 of 2
APPLICATION NO. : 10/491579
DATED                 : May 23, 2006
INVENTOR(S)      : Vittal et al.

It is certified that error appears in the above-identified patent and that said Letters Patent is hereby corrected as shown below:

| | |
|---|---|
| Column 2, Line 34 | Delete: "are" <br> Insert: -- is -- |
| Column 2, Line 67 | Delete: "shown below:" <br> Insert: -- shown below: formula IV -- |
| Column 4, Line 25 | Delete: "preferably in" <br> Insert: -- preferably be in -- |
| Column 4, Line 53 | Delete: "acetoxy)1-1-ethanone" <br> Insert: -- acetoxy)] – 1 -ethanone -- |
| Column 4, Line 66 | Delete: "for at" <br> Insert: -- at -- |
| Column 5, Line 36 | Delete: "charges" <br> Insert: -- charged -- |
| Column 5, Line 57 | Delete: "formula I" <br> Insert: -- formula I. -- |
| Column 6, Line 15 | Delete: "compound II" <br> Insert: -- compound II. -- |
| Column 6, Line 27 | Delete: "$SCH_3$." <br> Insert -- $SCH_3$-- |
| Column 6, Line 32 | Delete: "of for" <br> Insert: -- of -- |
| Column 6, Line 34 | Delete: "methyl thlo" <br> Insert: -- methyl thio -- |

UNITED STATES PATENT AND TRADEMARK OFFICE
CERTIFICATE OF CORRECTION

PATENT NO.       : 7,049,459 B2
APPLICATION NO.  : 10/491579
DATED            : May 23, 2006
INVENTOR(S)      : Vittal et al.

It is certified that error appears in the above-identified patent and that said Letters Patent is hereby corrected as shown below:

Column 6, Line 39    Delete: "1[((4-methylthio)
                     Insert: -- 1-[(4-methylthio) --

Signed and Sealed this

Twentieth Day of March, 2007

JON W. DUDAS
*Director of the United States Patent and Trademark Office*